US00PP31265P2

(12) United States Plant Patent
O'Neill

(10) Patent No.: US PP31,265 P2
(45) Date of Patent: Dec. 24, 2019

(54) ***BOUGAINVILLEA* PLANT NAMED 'VISTA5'**

(50) Latin Name: *Bougainvillea communis*
Varietal Denomination: Vista5

(71) Applicant: Jerome O'Neill, Juana Diaz, PR (US)

(72) Inventor: Jerome O'Neill, Juana Diaz, PR (US)

( * ) Notice: Subject to any disclaimer, the term of this patent is extended or adjusted under 35 U.S.C. 154(b) by 0 days.

(21) Appl. No.: 16/350,578

(22) Filed: Dec. 3, 2018

(51) Int. Cl.
*A01H 5/02* (2018.01)
*A01H 6/00* (2018.01)

(52) U.S. Cl.
USPC ..... Plt./256

(58) Field of Classification Search
USPC ..... Plt./226, 256
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Bougainvillea* cultivar named 'Vista5' is disclosed, characterized by white bracts with a pink mottled blush, a compact growth habit, and variegated foliage. The new variety is a *Bougainvillea*, typically produced as an ornamental plant.

2 Drawing Sheets

Figure 1:
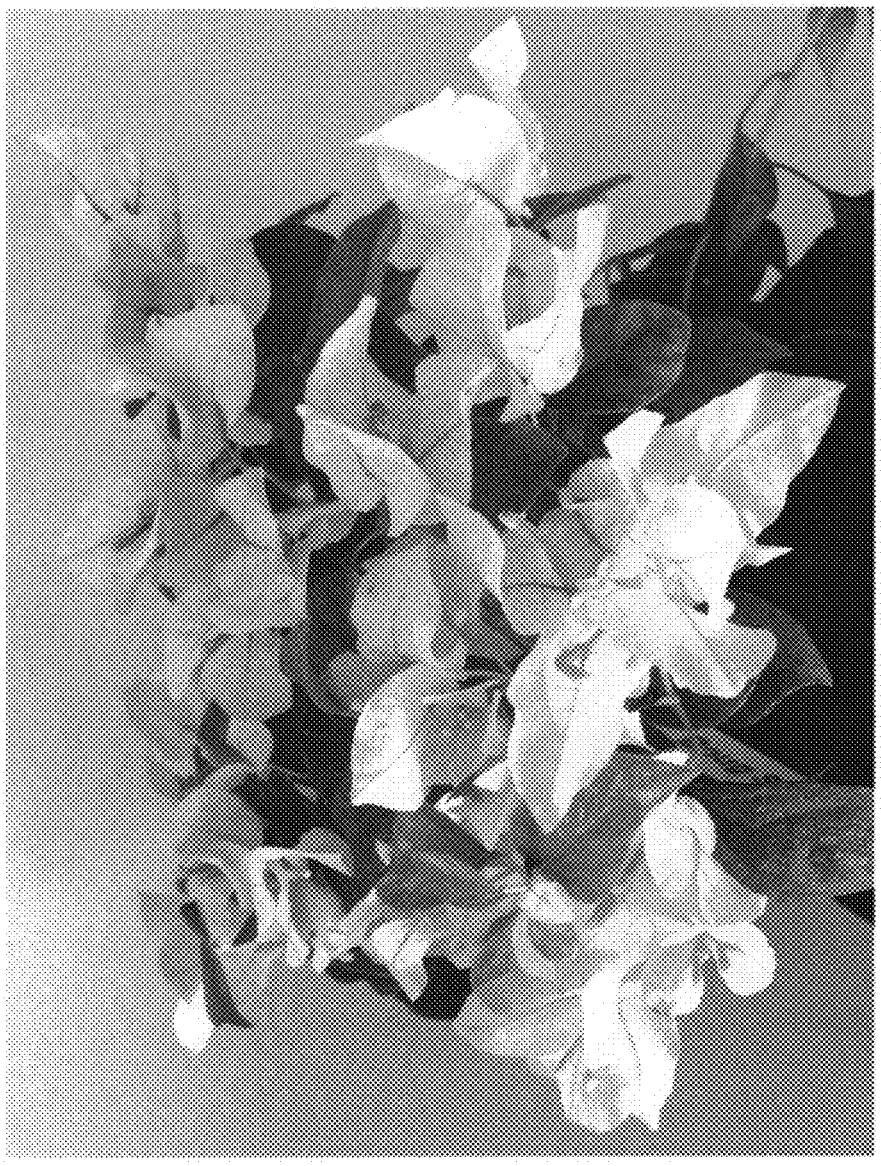

Latin name of the genus and species: *Bougainvillea communis*.

Variety denomination: 'Vista5'.

BACKGROUND OF THE INVENTION

The new cultivar is the product of chance discovery. The new variety originated as naturally occurring whole plant mutation of the patented variety *Bougainvillea communis* 'Vista4', U.S. Plant Pat. No. 29,609. The inventor discovered the variety in a commercial planting of the parent variety in Juana Diaz, Puerto Rico in March of 2016.

After identifying the interesting flower color mutation, the inventor observed the single plant mutation for several months. First propagation was performed by terminal vegetative cuttings at a commercial greenhouse during May of 2016, in Juana Diaz, Puerto Rico. Access to all plants was restricted, as plants were kept in a facility belonging to the inventor and not open to the public. Date of first sale was Jan. 12, 2018. This sale was made directly by the inventor or one who obtained the claimed invention directly or indirectly from the inventor. This sale and all public disclosures made before the filing of this application fall within the exception allowed under 102(b)(1).

Through subsequent propagation by vegetative cuttings, multiple generations have been reproduced, which have shown that the unique features of this cultivar are stable and reproduced true to type.

SUMMARY OF THE INVENTION

The cultivar 'Vista5' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Vista5'. These characteristics in combination distinguish 'Vista5' as a new and distinct *Bougainvillea* cultivar:

1. Variegated foliage.
2. White bracts with a pink mottled blush,
3. Compact growth habit.

PARENT COMPARISON

Plants of the new cultivar 'Vista5' are similar to the parent, in most horticultural characteristics. However, characteristics of the new cultivar differ in the following:

1. The new variety has white bracts with a pink mottled blush, while the parent has magenta bracts.
2. The new variety is less vigorous than the parent.

COMMERCIAL COMPARISON

Plants of 'Vista5' are similar in some horticultural characteristics to the variety *Bougainvillea* 'Yani's Delight', unpatented. The new variety, however, differs in the following:

1. The new variety has variegated foliage, 'Yani's Delight' does not.
2. The new variety has a more compact growth habit than this comparator.
3. 'Yani's Delight' has more pink blush coloration to the white bracts than 'Vista5'.

Plants of 'Vista5' are similar in some horticultural characteristics to the variety *Bougainvillea* 'Imperial Thai Delight', unpatented. The new variety, however, differs in the following:

1. The new variety has variegated foliage, 'Imperial Thai Delight' does not.
2. The new variety has a more compact growth habit than this comparator.
3. 'Imperial Thai Delight' has more pink blush coloration to the white bracts than 'Vista5'.

BRIEF DESCRIPTION OF THE PHOTOGRAPHS

The accompanying photograph in FIG. 1 illustrates in full color a typical plant of 'Vista5' grown outdoors at a commercial nursery in Juana Diaz, Puerto Rico. This plant is approximately 9 months old, shown in a 6 inch pot.

Figure 2:
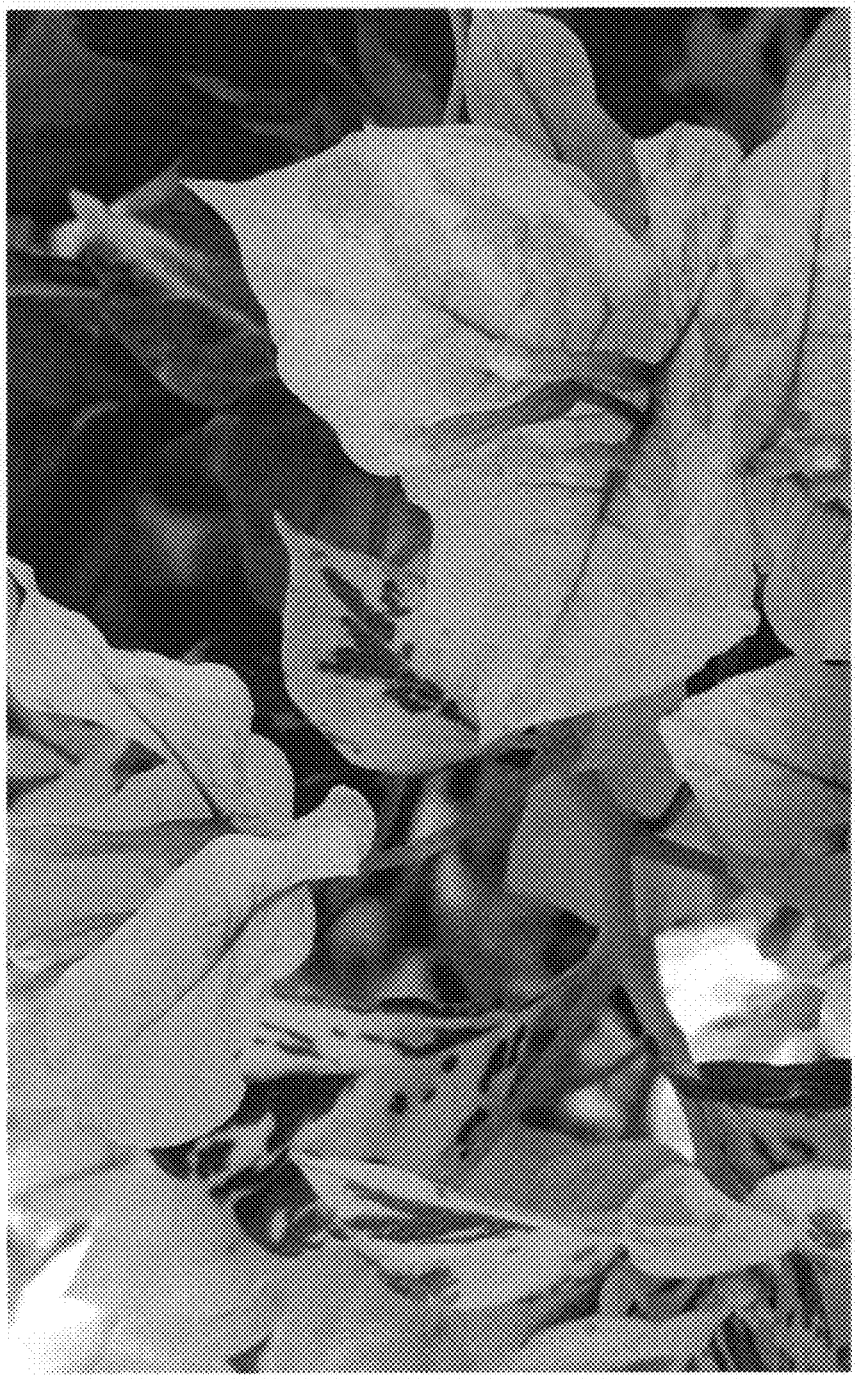

FIG. 2 illustrates a closer view of the foliage and flowering bracts.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe a 'Vista5' plant. This plant was grown in a greenhouse in a commercial 5.5-inch pot, in Juana Diaz, Puerto Rico. The plant described is approximately 6 months old and consists of 3 rooted cuttings in 1 pot. Temperatures ranged from 15° C. at night and 18° C. to 24° C. during the day. No artificial light, photoperiodic treatments were given to the plants. Measurements and numerical values represent averages of typical plant types.

Botanical classification: *Bougainvillea communis* 'Vista5'.

PROPAGATION

Time to initiate roots: 14-21 days at approximately 25° C.

Root description: Roots are fine, fibrous and well branched.

Time to produce a rooted plant: Approximately 6 to 12 weeks.

Root color: Near RHS Grey-Brown 199D and Greyed-Yellow 161D.

PLANT

Growth habit: This plant is an upright tender perennial, suitable for indoor ornamental use, or outdoor garden use in warm climates.

Pot size of plant described: 5.5 inch.

Height: 20 cm.

Plant spread: 27 cm.

Main stem color: Near RHS Grey 201C, underneath Brown 200B.

Main stem texture: Scaly.

Branching characteristics: Not free branching, moderate branching can be achieved with pinching.

Length of primary lateral branches: 10 to 15 cm.

Quantity of primary lateral branches: 2 to 3 per plant.

Characteristics of primary lateral branches:

*Diameter*.—Approximately 0.3 to 0.4 cm.

*Color*.—Near RHS Greyed-Green 197B.

*Texture*.—Rough, somewhat scaly.

Internode length: 0.7 cm to 1.3 cm.

FOLIAGE

Leaf:

*Arrangement*.—Alternate, simple.

*Quantity*.—Approximately 6 to 10 per branch on a 6 month old plant.

*Average length*.—Average range about 5.5 cm to 7.5 cm.

*Average width*.—Average range about 2.9 cm to 3.7 cm.

*Shape of blade*.—Obovate.

*Apex*.—Acute.

*Base*.—Obtuse.

*Margin*.—Entire.

*Texture of top surface*.—Smooth.

*Texture of bottom surface*.—Smooth.

*Appearance of top surface*.—Matte.

*Appearance of bottom surface*.—Matte.

*Color*.—Young foliage upper side: Variegated near RHS Green 143B and Yellow-Green 154D and Green-Yellow 1D. Young foliage under side: Variegated near RHS Green 143B and Yellow-Green 154D. Mature foliage upper side: Near RHS Green 137A, center variegation near Yellow-Green 154C. Mature foliage under side: Near RHS Green 143B, slightly variegated 154D.

*Venation*.—Type: Pinnate. Venation color upper side: RHS Yellow-Green 154D. Venation color under side: RHS Yellow-Green 154C.

*Petiole*.—Length: Average 1.5 cm to 3.2 cm. Diameter: 0.2 cm. Color: Near RHS Yellow-Green 144C. Texture: Smooth.

Other characteristics:

Thorns: Thorn density is minimal. One thorn occurs above a node. A thorn is not always present, sometimes no thorn above leaf or node. Thorn is pointed upwards; young thorns are more flexible and less sharp. Old thorns are very sharp, strong and woody.

*Average thorn length*.—Mature thorn approximately 1.0 cm.

*Average thorn width at base*.—0.2 cm.

*Shape*.—Needlelike.

*Thorn curvature*.—None, straight.

*Thorn coloration*.—Young thorns not observed. Old thorns RHS Greyed-Green 197B.

FLOWER

Normal flowering period: Continuously from early Spring through Fall in Puerto Rico.

Inflorescence:

*Form*.—Axillary, compact cyme.

*Width of entire inflorescence*.—Average 12.0 cm.

*Height of entire inflorescence*.—Average 6.0 cm.

*Quantity of individual flowers in inflorescence*.—Average 9 on a 6 month old plant.

Flower longevity on plant: Approximately 10 days.

Quantity of inflorescence per plant: Average 4 to 8.

Quantity of bract clusters: Very dense. Average range 9 to 12 on a 6 month old plant.

Persistent or self-cleaning: Self-cleaning.

Bud:

*Shape*.—Oblanceolate.

*Length*.—0.9 cm.

*Diameter*.—0.3 cm.

*Color*.—Near RHS Green-White 157A. Veins Yellow-Green 145C.

Individual true flower:

*Form/type*.—Single, tubular flowers growing from the base of a single bract. The flowers have no petals or sepals. The individual true "flower" is small, and each cluster of three flowers is surrounded by three bracts. Sometimes the cluster consists of more flowers but the number of bracts is nearly always 3.

*Diameter.*—0.7 cm.
*Length.*—1.7 cm.
*Days lasting on plant.*—Approximately one week.

Petals: 5 petals fully fused into a long tubular symmetrical flower, outwardly flared at apex.
*Tip.*—Acute.
*Base.*—Fused.
*Margin.*—Unfused upper-section crenate.
*Color.*—Upper section, immature: RHS Yellow-White 158D. Tube immature outside surface: RHS Yellow-Green 145C. Tube immature inside surface: RHS Yellow-Green 145C. Upper section, mature: RHS Yellow 2D. Tube mature outside surface: RHS Yellow-Green 145C. Tube mature inside surface: RHS Yellow-Green 145C.

Bracts:
*Days lasting on plant.*—Approximately 10, self-cleaning.
*Type.*—Single.
*Shape.*—Ovate.
*Length.*—3.5 cm.
*Width.*—2.5 cm.
*Tip.*—Acute.
*Base.*—Truncate.
*Margin.*—Entire.
*Aspect.*—Moderately undulating.
*Color.*—Under side of immature bract: RHS White 155A. Mid vein near Yellow-Green 145B. Lateral veins faintly flushed near Red-Purple 58B. Upper side of immature bract: RHS White 155A. Mid vein near Red-Purple 61B. Lateral veins faintly flushed near Red-Purple 58B. Under side of mature bract: RHS White 155A faint mottled blush near Red-Purple 70B. Mid vein Yellow-Green 145B. Veins flushed near Red-Purple 64B. Upper side of mature bract: RHS White 155A, mottled blush near Red-Purple 70B. Veins near Red-Purple 64B.

Sepals: No sepals observed.

Peduncles:
*Length.*—Average 2.2 cm.
*Diameter.*—0.2 cm.
*Angle.*—Approximately 45° to the lateral branch.
*Strength.*—Strong.
*Texture.*—Smooth.
*Color.*—Near RHS Yellow-Green 145A, flushed 70C.

Pedicels:
*Arrangement.*—Individual flowers in whorls of 3, together on pedicels. Each individual flower sessile, implanted in a colorful bract.
*Length.*—1.7 cm.
*Diameter.*—0.2 cm.
*Angle.*—Average angle of 75 degrees.
*Strength.*—Moderately strong.
*Color.*—Near RHS Yellow-Green 145B.

Fragrance: None.

REPRODUCTIVE ORGANS

Stamens:
*Number.*—Average 8.
*Length.*—5 mm.

Anthers:
*Length.*—Approximately 0.5 mm.
*Color.*—Near Yellow-Orange 18A.
*Pollen.*—Color RHS Yellow-Orange 20A. Quantity: Scant.

Pistil:
*Number.*—1.
*Length.*—8 mm.
*Style.*—Length: 7 mm. Color: RHS Yellow-Green 145D.
*Stigma.*—Shape: Linear. Color: Near RHS Yellow 13B. Ovary Color: Near RHS Yellow Green 145C.

OTHER CHARACTERISTICS

Seeds and fruits: Seed production not observed.

Disease/pest resistance: Neither resistance nor susceptibility to diseases or pests has been observed in this variety.

Drought tolerance: No drought tolerance. Leaves and bracts will drop off the plant immediately under dry conditions.

What is claimed is:

1. A new and distinct cultivar of *Bougainvillea* plant named 'Vista5' as herein illustrated and described.

* * * * *